United States Patent [19]

Isaacson et al.

[11] Patent Number: 4,773,422

[45] Date of Patent: Sep. 27, 1988

[54] SINGLE CHANNEL PULSE OXIMETER

[75] Inventors: Philip O. Isaacson, Chanhassen; David W. Gadtke, Maple Grove; Vernon D. Heidner, Mound; Neal F. Nordling, White Bear Lake, all of Minn.

[73] Assignee: Nonin Medical, Inc., Plymouth, Minn.

[21] Appl. No.: 44,329

[22] Filed: Apr. 30, 1987

[51] Int. Cl.⁴ .............................................. A61B 5/00
[52] U.S. Cl. ..................................... 128/633; 128/665
[58] Field of Search ................ 128/632.3, 664.7, 673, 128/675, 689, 748; 356/39-41

[56] References Cited

U.S. PATENT DOCUMENTS

| | | | |
|---|---|---|---|
| 3,980,075 | 9/1976 | Heule | 128/666 |
| 4,167,331 | 9/1979 | Nielsen | 128/633 X |
| 4,266,554 | 5/1981 | Hamaguri | 128/633 |
| 4,353,152 | 10/1982 | O'Connor et al. | 128/689 |
| 4,407,290 | 10/1983 | Wilber | 128/665 X |
| 4,586,513 | 5/1986 | Hamaguri | 128/633 |
| 4,592,361 | 1/1986 | Parker et al. | 128/633 |
| 4,651,741 | 3/1987 | Passafaro | 128/633 |

Primary Examiner—Kyle L. Howell
Assistant Examiner—Angela D. Sykes
Attorney, Agent, or Firm—Orrin M. Haugen; Thomas J. Nikolai; Frederick W. Niebuhr

[57] ABSTRACT

An electronic apparatus for sensing the percentage of different blood constituents in arterial blood. Light of a plurality of separate wave lengths is sequentially made to pass through a portion of the body, either by direct transmission or scattering so that the pulsatile blood flow modulates the intensity of the light. A signal processing circuit functioning in accordance with the Lambert-Beer Law is used to determine the percentage of different blood constituents from the fluctuations component of the logarithm of the light absorption. The sampling of the separate wave lengths is time-multiplexed through a common channel, thus obviating the need for a separate channel of similar electronics for each constituent to be monitored. The signal processing circuitry is also effective to compensate for noise due to ambient light or other stray sources, thus improving the overall accuracy.

11 Claims, 3 Drawing Sheets

SINGLE CHANNEL PULSE OXIMETER

BACKGROUND OF THE INVENTION

I. Field of the Invention: This invention relates generally to medical instrumentation, and more particularly to an electronic device for measuring and indicating the percentage of one or more constituents of arterial blood.

II. Discussion of the Prior Art: Various systems are disclosed in the prior art for measuring the percentage of various constituents in arterial blood. For example, in the Wilber U.S. Pat. No. 4,407,290 assigned to Biox Technology, Inc., of Boulder, Colo., there is described an oximeter which can be used, non-invasively, for measuring the ratio of oxygenated hemogloblin in arterial blood by providing first and second light sources of differing wavelength which shine light through a body member with the transmitted or reflected light being picked up by a photo detector. The signal picked up by the detector is effectively modulated by the pulsatile flow of blood through the area being sensed, and then the pulse train is divided into separate channels in which further signal processing operations are performed. The Biox device thus requires a number of channels of substantially similar electronic devices equal to the number of light sources required to uniquely identify the constituents being measured. Generally speaking, the number of radiation sources of different wavelength needed to measure n constituents is n+1. This replication of electronic circuitry in plural channels naturally increases the cost of the instrument and also can adversely affect the device's accuracy, given the fact that component values in one channel can shift with time relative to corresponding components in another.

The Nielsen U.S. Pat. No. 4,167,331 assigned to the HewlettPackard Company of Palo Alto, Calif., likewise describes a pulse oximeter in which plural light sources are sequentially turned on an off and transmitted through a body part in which arterial blood flows. The transmitted or reflected (scattered) light is picked up by a photo-sensitive device and the resulting pulse modulated signal is fed through a logarithmic amplifier to produce a voltage which is a logarithmic function of the current from the sensor. This voltage is then divided so as to be processed by separate signal processing hardware in separate individual channels, the number of channels corresponding to the number of blood components (and individual light sources) employed in the system. Thus, like the Biox device, the Hewlet-Packard device also tends to be costly as the number of channels increases.

The Biox and Hewlett-Packard devices also are subject to error introduced by extraneous light sources or other noise which is picked up by the photo detecting device and fed through the plural channels along with the desired signal produced by the separate light sources utilized in the apparatus. Such extraneous light sources have been known to impact the accuracy of the instrument by as much as ten percent or even more.

OBJECTS

It is a principle object of the present invention to provide a device for non-invasively measuring and indicating the percentage level of various constituents in arterial blood.

Another object of the invention is to provide a pulse oximeter which is simpler in its design and implementation than known prior art systems.

Yet another object of the invention is to provide a pulse oximeter not only having a lower cost of manufacture but of significantly increased accuracy over known prior art systems currently available in the marketplace.

Still another object of the invention is to provide a pulse oximeter which is designed to effectively exclude adverse effects due to noise and other ambient or surrounding conditions at a point in the circuit which obviates the need for extensive and costly filtering or other remedial circuit configurations.

SUMMARY OF THE INVENTION

In accordance with the present invention, a plurality of light sources of differing wavelengths are provided and are switched on and off in accordance with a desired program via control signals emanating from a microprocessor. The light (radiation) from the multiple sources is sequentially directed along a common path through a portion of the body and a photo-detector is used to produce an electrical output proportional to the intensities of the light transmitted through the body as well as a contribution due to background noise, including ambient light. A specially designed logarithmic amplifier is connected to receive the photo-detector output and functions to provide a voltage proportional to the logarithm of the net of the total received signal less the background and ambient signal contributions. The voltage signal is suitably amplified to compensate for differing D.C. offsets of the sequential signals occasioned by the switching of the plural light sources in such a way that a single channel may be used for further process those signals. More particularly, an analog-to-digital converter circuit of a unique design converts the output from the pulse amplifier into a digital format and the digitized signals are applied to a microprocessor suitably programmed to perform band-pass filtering, peak-to-peak measurements and, ultimately, the constituent determination computation. The output from the microprocessor may be used to generate audio/visual alarms either at the instrument or remotely therefrom. Furthermore, the computer output may be converted to an analog form and used to drive a strip recorder for a hard-copy presentation. Alternatively, the output information can be directly displayed on a suitable LED, liquid crystal or CRT device.

In that in practical applications, the signal from the photo-detector consists of a superposition of the signal due to the intended light source, signals from ambient light and signals from leakage current sources in the circuitry and photo-detector, the design of the present invention includes means for removing the extraneous background signals so that only a voltage proportional to the logarithm of the light signal is provided to the downstream signal processing circuitry. The design also requires only a single channel for sequentially processing the signals from all of the plural light sources of differing wavelengths.

The foregoing objects, features and advantages of the invention will become more clear to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
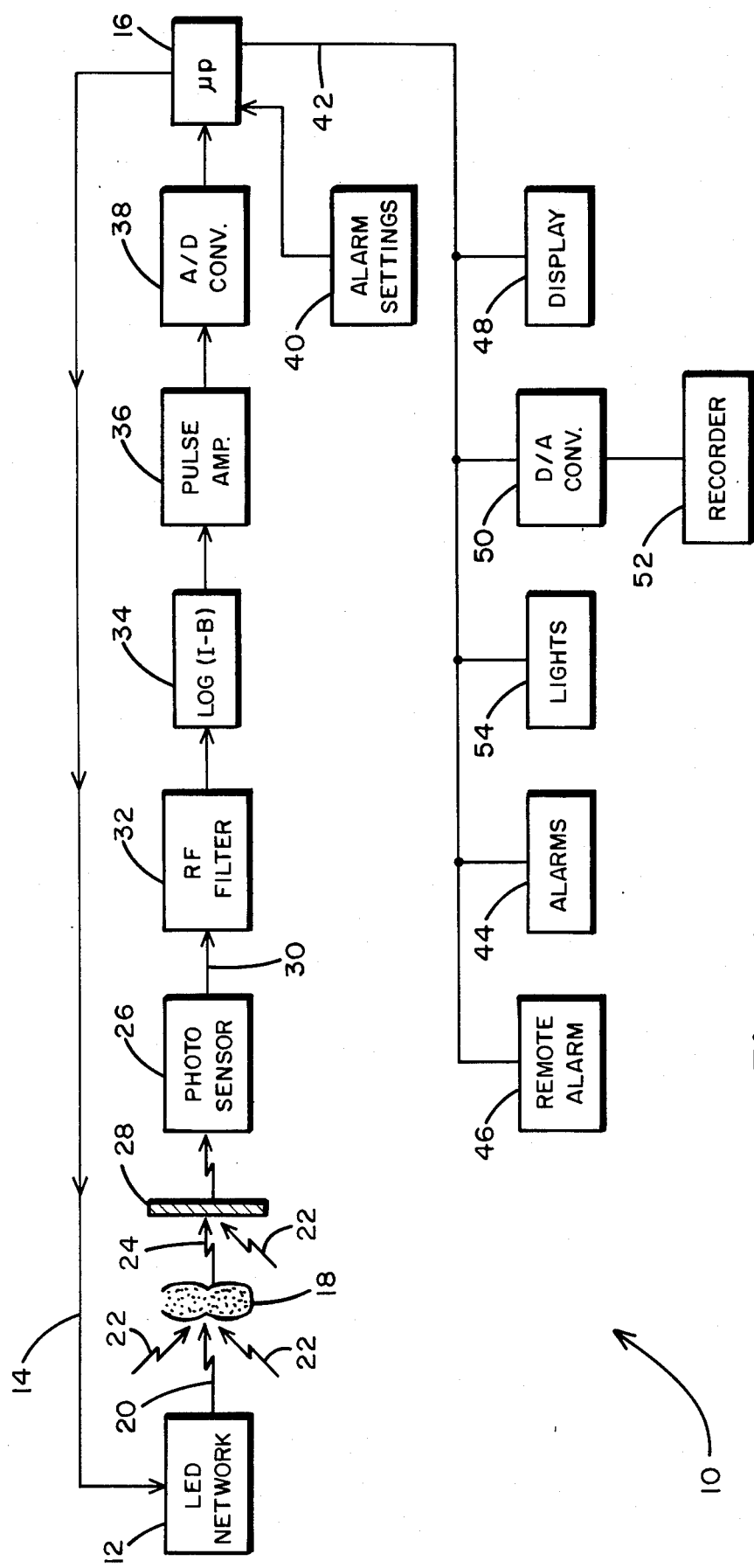
FIG. 1 is a block diagram of the preferred embodiment of the invention.

Referring to FIG. 1, there is illustrated a general block diagram of the overall device constructed in accordance with the present invention. The blood constituent analyzer is indicated generally by numeral 10 and is seen to include a source of light energy 12 which includes two or more sources of radiation, preferably light-emitting diodes (LEDs), which are arranged to be switched on and off sequentially rather than in parallel by control timing signals applied to them via a control line 14 emanating from a microprocessor 16. As is well known in the art, a pulse oximeter is a device for detecting the percentage $O_2$ saturation of the blood. Two separate light sources are required in its implementation, one emitting light in the red portion of the visible spectrum and the other emanating in the infrared portion of the spectrum. As earlier indicated, when a plurality of different blood constituents are to be measured, the number of light sources required is one greater than the numer of such constituents. The light energy from the LED network 12 is optically coupled to a body part, such as a patient's finger, the finger being identified by numeral 18. The light from the desired light sources in the network 12 is represented by the light ray 20 while extraneous ambient light is represented by the rays 22. Both the desired component and the extraneous or background component then pass through the body part 18 as indicated by the ray 24. It is also possible that ambient light may reach the sensor without first passing through body tissue. While in the configuration of FIG. 1, the light is shown as being transmitted through the body member, it is, of course, possible to locate the optical sensor on the same side of the body member as the light source and in that configuration, light energy reflected or scattered by the pulsatile blood flow through the body part is what is picked up by the sensor.

With continued reference to FIG. 1, the photo pickup or sensor device is indicated by numeral 26 and typically may be a suitable photo-diode, many types of which are known in the art. In an effort to reduce the amount of ambient or background light reaching the photo-sensor, it is found convenient to incorporate a suitable light filter, as at 28, designed to block out most of the light in the visible range while transmitting the red and infrared wavelengths therethrough. A so-called Wratten filter is admirably suited to the instant application.

The output from the photo sensor 26 appearing on line 30 is thus a pulse modulated current of two discrete amplitudes: (1) the component of that signal due to the passage of the longer wavelength light (infrared) and (2) the component due to the shorter wavelength light (red). The modulation envelope on these signals is due to the pulsatile flow of blood in and out of the body member 18 due to the beating action of the patient's heart. Thus, the current signal emanating from the photo sensor 26 and appearing on line 30 is a composite due to the switched light sources and due to the ambient light as well as any noise developed internal to the photo sensor circuitry 26 itself. This signal waveform is then applied to a suitable RF low-pass filter 32 which is included to filter out any radio frequency interference which might be present in the environment in which the system of the present invention is used. For example, when the pulse oximeter of the present invention is to be used in an operating room environment, the low-pass filter 32 may effectively filter out RF interference which might be generated by electrocautery equipment or the like. As such, the cut-off frequency of the low-pass filter 32 might typically be set in the range of from 100 to 300 KHz, although limitation to this particular frequency is not intended. In that various forms of discrete component low-pass RLC filters for RF signals are known in the art, it has not been felt necessary to specifically depict and describe such a device.

Figure 2:
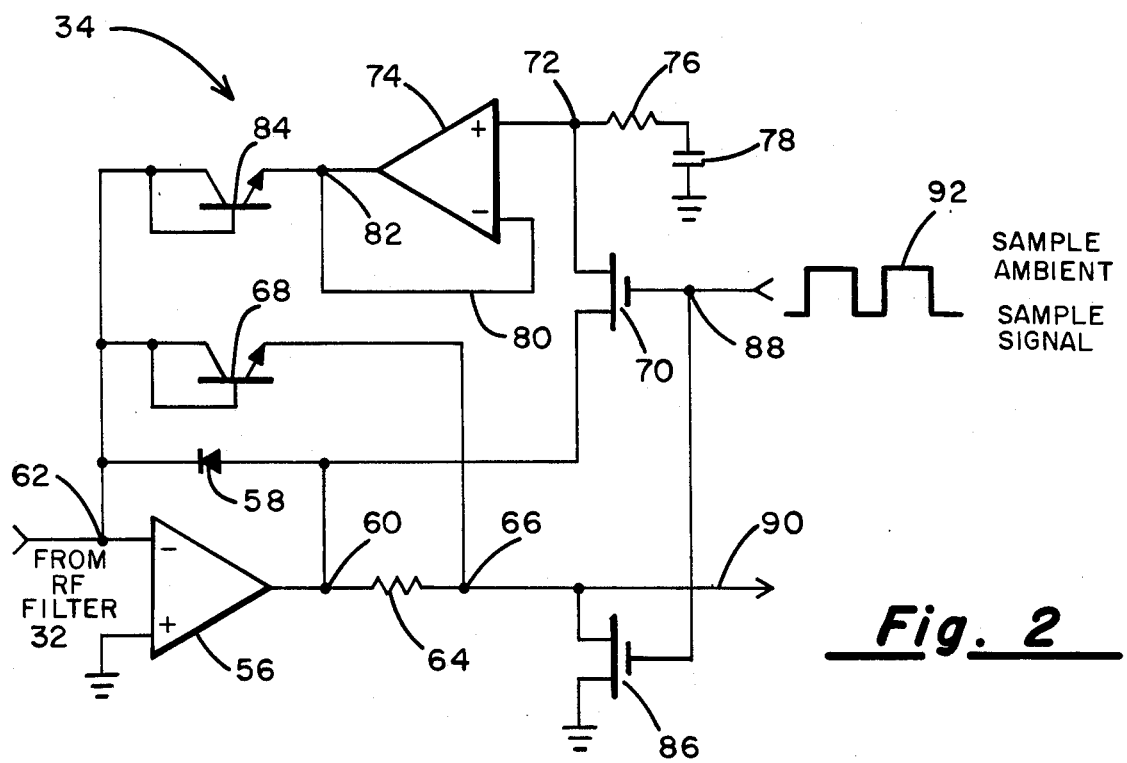
FIG. 2 is an electrical circuit diagram of the preferred logarithmic amplifier used in the system of FIG. 1.

The signals emanating from the RF filter 32 are next applied to a specially designed logarithmic amplifier 34. As will be later described in greater detail when the implementation of FIG. 2 is explained, the logarithmic amplifier 34 is specially designed to subtract off the signal components due to the ambient light or background (B) from the current component (I) which is due to the red and infrared LED light sources in the network 12. Because of the unique design of the logarithmic amplifier used herein, the resulting output signal is a voltage directly proportional to the logarithm of the input current, but with the component due to background noise, including ambient light, removed therefrom.

The signal output from the logarithmic amplifier 34 is next applied to a pulse amplifier circuit 36, also of unique design. As was pointed out in the introductory portion of this specification, one of the key aspects of the present invention is the elimination of the need for plural signal processing channels and attendant replication of signal processing circuitry in each of these channels. As will be further explained in considerable detail, it is the design of the pulse amplifier 36 used herein that permits the time multiplexed sharing of a single channel of downstream electronics. To do this, pulse amplifier 36 must function to effectively amplify only the AC components, i.e., the modulating envelopes while subtracting out the DC levels on which the AC component is superimposed, i.e., the offset. Thus, the AC signal containing the information and contributed individually by the separate light sources is maintained in the same amplitude range, allowing the downstream A/D converter 38 to digitize both samples.

The analog-to-digital converter 38 is designed to provide an output whose pulse width is proportional to the amplitude of the input signal. The microprocessor 16 receives this variable width pulse and, using a suitable counting technique, converts it to a multi-bit digital representation so that it can be treated as an operand during the execution of the software instructions stored within the memory portion of the microprocessor 16.

The microprocessor 16 is specifically programmed to execute a series of signal processing steps on the thus formed operands. In particular, the input to the microprocessor is hipass filtered, which is effective to minimize artifacts such as from body movements, and following that, peak-to-peak measurements may be made with the peak information allowing subsequent rate measurement and the peak-to-peak amplitude being used to determine the percentage of a given constituent.

In a typical system, it is desired to provide an alarm when a constituent percentage, such as $O_2$ saturation of the hemoglobin, falls below some threshold value. The threshold may be entered into the microprocessor 16 by appropriate setting of the hard-wired switches represented by block 40 in FIG. 1. The microprocessor 16 is also shown as configured to provide signals over the bus 42 for initiating either an audible alarm 44 packaged within the oximeter housing itself or, alternatively, also providing an alarm at a remote location, such as a nursing station or the like, via alarm 46. The computer 16 may also drive a suitable alpha/numeric display device 48, such as a seven-segment display implemented either with LEDs or liquid crystal media. This display would typically be presented on the face plate of the housing containing the circuitry of the pulse oximeter.

It is also envisioned that digital output from the microprocessor 16 may be routed through a D/A converter 50 to create an analog representation of the quantity being measured and that analog representation can then be recorded on a strip recorder 52, thereby providing a hard-copy output.

Finally, the microprocessor 16, by providing appropriate control signals over bus 42, can illuminate one or more indicator lights 54 to reflect the operating state of the equipment or to signal the condition for which an alarm may be sounded.

Having described in detail the general organization of the preferred embodiment of this invention, consideration will next be given to the implementation of the non-conventional circuits employed so that persons of ordinary skill in the art will be in a position to construct and use the invention.

FIG. 2 shows a preferred implementation of the log (I-B) circuit 34 of FIG. 1. As mentioned, this circuit is specifically designed to eliminate the signal component emanating from the RF filter 32 which is due to ambient light from the desired components attributable to the red and infrared LED light sources in network 12. This composite signal is applied to the inverting input of a high gain operational amplifier 56 whose non-inverting input is tied to ground. A semiconductor diode 58 is employed as a feedback element for protection of the circuit against out-of-range reverse voltage signals and, as such, couples the output junction 60 of the operational amplifier 56 back to its inverting input terminal 62. A resistor 64 is coupled in series between the junction 60 and a junction point 66 and coupled between the junction point 66 and the inverting input terminal 62 of the operational amplifier 56 is a NPN transistor 68 connected to function as a diode by having its collector and base electrodes tied in common to the inverting input of op amp 56.

The output from op amp 56 is also coupled through a FET switch 70 to a junction point 72 which is common to the non-inverting input of a unity gain operational amplifier 74 and to a RC network, including resistor 76 and capacitor 78, one terminal of the capacitor 78 being connected to ground. A conductor 80 joins the output terminal 82 of the operational amplifier 74 back to its inverting input. A further NPN transistor 84, whose collector and base electrodes are commonly coupled, is connected between the output terminal 82 of the unity gain amplifier 74 and the inverting input terminal 62 of the high gain amplifier 56. A further FET switch 86 is included which has its gate electrode coupled to a common junction 88 with the gate electrode of the FET switch 70, its source electrode connected to the output line 90 and its drain electrode coupled to ground.

In operation, since the operational amplifier 56 has a very high impedance, practically no current flows into the op amp 56 itself. Instead, all of the input current coming from the RF filter 32 must either flow through the diode connected transistor 68 or the diode connected transistor 84. These transistors are being used as logarithmic elements, such that the voltage across one or the other of transistors 68 and 84 is proportional to the logarithm of the current flowing through it. In normal use, without the compensation circuit yet to be described, all of the current flowing into the junction 62 would be flowing through the transistor 68 and, thus, the output voltage appearing at junction 66 would be proportional to the log of the current flowing into junction 62. This current would be a composite of the components due to the light sources in network 12 (FIG. 1) as picked up by the photo sensor 26 plus the leakage currents developed within the circuit components themselves and the currents due to ambient or background light.

During the time intervals when the red and infrared light sources are turned off, a signal from the microprocessor indicated by wave form 92 turns on the FET switches 70 and 86. FET 86 thus assures that the voltage at junction 66 will be zero and, thus, there will be no current flowing through the transistor 68. With FET 70 conducting, the direct output signal from operational amplifier 56 is applied to the non-inverting input of operational amplifier 74. Through the feedback action of operational amplifier 56, which is running at a high gain while operational amplifier 74 is operating with a unity gain factor, the op amp 74 functions as a buffer to source or sink the current into it. Thus, the voltage developed across semiconductor device 84 is such that all of the current flowing through transistor 84 will be sinked by operational amplifier 74. That current, of course, is all of the current flowing into the input junction 62.

Immediately before turning on one of the LEDs in the network 12, the microprocessor applies a signal to the gate electrodes of the FET switches 70 and 86, as represented by the wave form 92, so that both of these FETs are non-conducting. Now, the sample-and-hold network comprising resistor 76 and capacitor 78 will maintain the voltage that had been present on the input to amplifier 74 so that the output voltage therefrom does not change and the same current flow is maintained through the semiconductor device 14. Considering that all of the current picked up by the photo sensor 26 due to ambient light and background noise is flowing through semiconductor device 84, when the appropriate LED light source in network 12 is turned on and there is thus an additional current flowing through the photo detector, that current component will flow through semiconductor device 68 and, as such, only the logarithm of the current from the desired light source will be present at node 66. All of the currents due to noise and ambient background light will have been removed from the current flowing through the output conductor 90. It can be seen then that the log (I-B) circuit 34 is effective to remove from the signal to be further processed all components due to ambient background light and currents due to extraneous noise developed in the photo detector 26.

Figure 3:
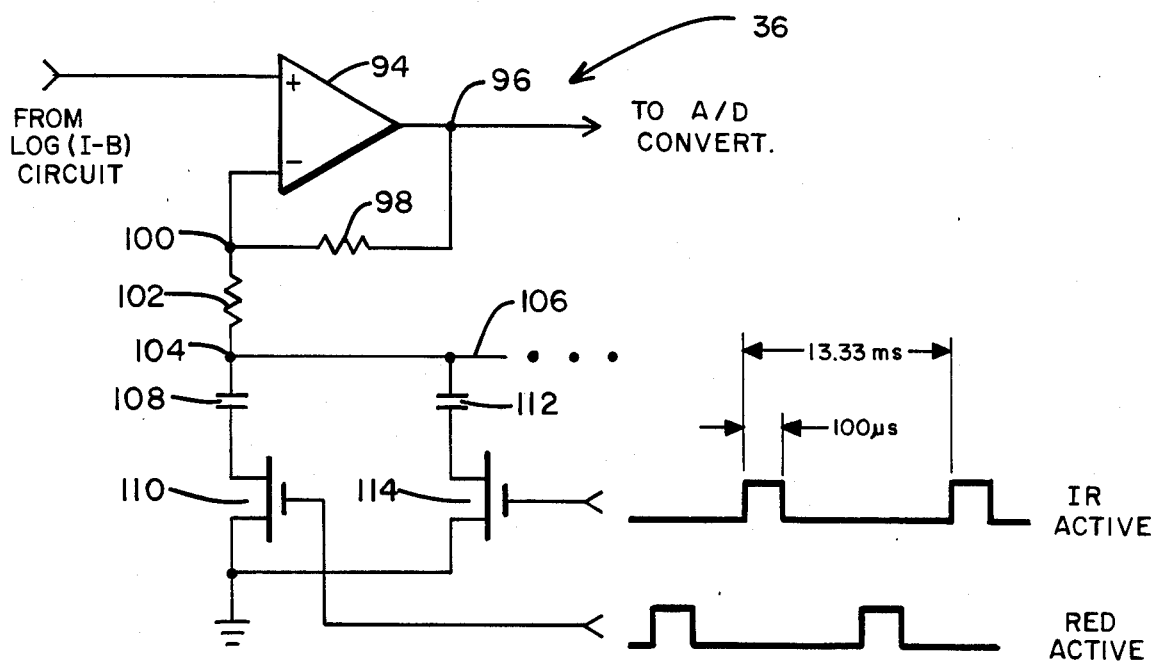
FIG. 3 is a circuit diagram of a preferred pulse amplifier used in the circuit of FIG. 1.

Referring next to FIG. 3, an explanation will be given of the makeup of the pulse amplifier 36, the use of which allows a single channel architecture to the overall pulse oximeter design. The function of the amplifier 36 is to provide level compensation for multiple sequential signals. The sequential signals themselves arrive from the log (I-B) circuit 34 and are applied to the non-inverting input of an operational amplifier 94. The output from amplifier 94 appearing at junction 96 is fed back through a resistor 98 to the inverting input to that amplifier, which is coupled to junction point 100. A further resistor 102 is coupled between junction 100 and junction 104 to which a plurality of series-connected capacitors and FET switches are also joined by way of a conductor or bus 106. The number of capacitor/FET combinations is determined by the number of blood constituents to be monitored. It will be recalled that where only the saturation level of $O_2$ is of interest, two light sources are sufficient and, thus, two series-connected capacitor/FET combinations are required. Specifically, a capacitor 108 is connected in series with the source or drain electrode of a FET 110 whose other electrode is tied to ground. The gate electrode of FET 110 is coupled to receive timing or gating pulses from the microprocessor corresponding to the on/off state of the LED devices used in network 12. Likewise, a capacitor 112 is connected in series with the source or drain electrode of a FET 114 whose other electrode is also tied to ground. The gate electrode of FET 114 also receives a gating signal from the microprocessor corresponding to the on/off state of a particular one of the LED device in network 12. The component value of resistor 98 is much greater than that of resistor 102 and, as such, amplifier 94 provides unity gain for DC levels while the gain for fluctuating components may typically be approximately 100. Thus, when the red LED device is active, the alternating component of the logarithmic output from the circuit 34 due to the pulsatile blood flow through the body member in question will be highly amplified while the DC level on which this fluctuating component appears is suppressed. Similarly, when the IR LED is active and FET 114 is turned on, the alternating component due to modulation of the IR component of current occasioned by pulsatile blood flow will be amplified. Likewise, if additional blood constituents are to be monitored and additional series connected capacitor/FET circuits are coupled in parallel between bus 106 and ground, the particular component due to the activated light source will be amplified while its DC component will remain unaffected by the level compensation circuit 36.

By observing the gating wave forms applied to the gates of the FETs 110 and 114, it will be noted that they do not overlap. In fact, the timing is such that the FETs are not turned on until after the associated LED is turned on and the circuit has stabilized.

The RC time constant of the resistor 102 and the capacitors 108, 112, etc. determines the effective time constant which, when considered in connection with the duty cycle of the gating pulses, determines where the AC gain of the op amp 94 begins to drop off towards unity. As indicated in the drawings, the gating pulses themselves may be approximately 100 microseconds in length with the period being approximately 13.33 milliseconds, corresponding to a switching rate of 75 Hz.

Because the amplifier circuit 36 is designed to sequentially amplify the independent components of the signal train occasioned by the sequential energization of the light sources, the need for plural signal processing channels is obviated. This is a clear advantage over prior art systems which require a separate set of signal processing components for each channel where the number of channels is equal to the number of light sources involved. For example, one such pulse oximeter sold by the Hewlett-Packard Company and which is believed to embody the design reflected in the aforereferenced U.S. Pat. No. 4,167,331, involves 17 channels which must be perfectly matched in terms of gain and which, therefore, requires frequent and precise adjustment of many potentiometers and the like to compensate for component drift and other component aging phenomena. A single channel approach such as in the present invention totally obviates this problem and affords a clear advantage.

Figure 4:
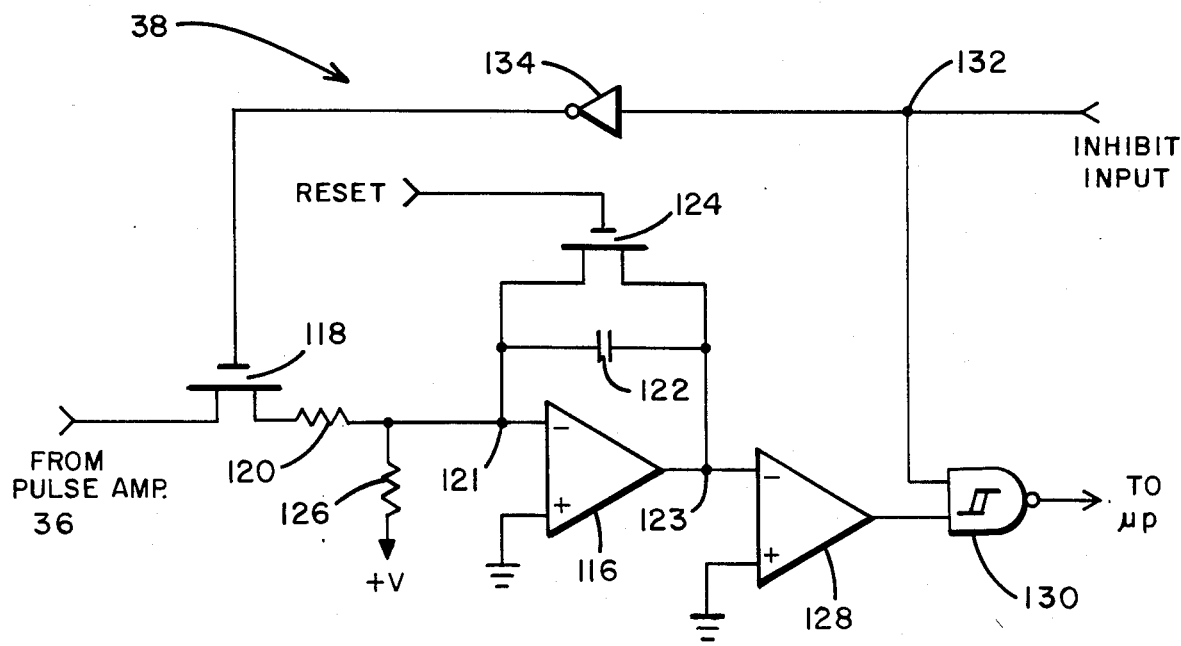
FIG. 4 is a circuit diagram of the analog-to-digital converter portion of the circuit of FIG. 1.

The A/D converter 38 shown in FIG. 4 comprises a dual slope integrator which includes a first operational amplifier 116 whose non-inverting input is tied to ground and whose inverting input is adapted to receive the output from the pulse amplifier 36 via a switching FET 118 and a series coupled resistor 120. The operational amplifier 116 is provided with a feedback circuit including an integrating capacitor 122 which is shunted by a further FET switch 124. When performing its signal integrating function, the switch 124 is open but when it is desired to reset the integrator, an appropriate pulse turns on the FET switch 124 to short out the integrating capacitor 122.

The inverting input of the op amp 116 is provided with a positive bias via voltage source $+V$ and a series connected resistor 126.

The output from the integrating amplifier 116 is applied to the inverting input of a further op amp 128 whose non-inverting input is also tied to ground. The output from op amp 128 acts as a threshold comparator and is coupled to a first input of a NAND gate 130 and the second input to that gate comprises an "inhibit input" signal applied to junction 132 from the microprocessor. This "inhibit input" signal is inverted at 134 and the inverted signal is applied to the gate electrode of the switching FET 118 as illustrated.

Figure 5:
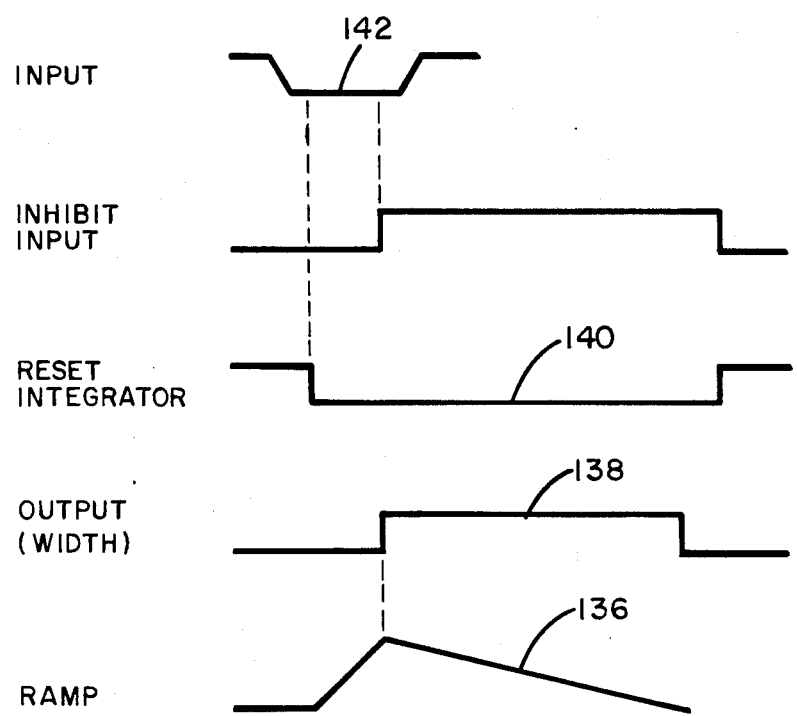
FIG. 5 depicts a series of timing diagrams useful in understanding the mode of operation of the analog-to-digital converter circuit of FIG. 4.

To better understand the operation of the circuit of FIG. 4, reference is made to the timing wave forms illustrated in FIG. 5. The integrator comprising op amp 116 and its feedback capacitor 122 operates in a well known fashion to integrate the current flowing into junction point 121, which is either via the resistor 120 or the resistor 126. When an input signal from the pulse amplifier 36 is present, integration of the signal takes place when the FET 118 is turned on. The input signal current charges the capacitor 122 in such a way that the output from the amplifier 116 is proportional to the amplitude of input signal and the time that the transistor 118 is turned on. Transistor 118 is turned on for a fixed period of time and, thus, the voltage at junction 123 will be proportional to the input voltage from the pulse amplifier. Having sampled and integrated the input signal, transistor 118 is next turned off by the "inhibit input" signal fed through the inverter 134. At this point, capacitor 122 begins to discharge through resistor 126 to the $+V$ source. The time it takes for the capacitor to discharge back to zero is, therefore, proportional to the amount of voltage which was across the integrating capacitor 122 and, as indicated earlier, that voltage is proportional to the input signal from the pulse amplifier 36. The ramp down of the integrating capacitor is identified numeral 136 in FIG. 5 and is seen to define the length of the output signal 138. The reset signal applied to FET 124 is indicated by waveform 140 and it can be seen that the transistor 124 is turned on to hold a zero voltage condition across capacitor 46 until such time as the integration operation is to begin. The reset is not released until after the input signal 142 has stabilized. The delay between the start of the input signal and the release of the reset is controlled by the microprocessor. In a similar fashion, the FET 118 is turned off before the end of the input signal where it begins to fall off.

At the time that the microprocessor generates the "inhibit input" signal, it also initiates an internal timer which continues to run until the ramp 136 reaches its zero-crossing point as determined by op amp comparator 128 and, thus, the count developed in the timer will be proportional to the amplitude of the input signal. It can be seen, then, that the circuit of FIG. 4 is capable of performing an amplitude-to-pulse width conversion on the signal arriving from the pulse amplifier 36 and that, in combination with the internal circuitry of the microprocessor (not shown), allows the pulse width to be digitized, forming a multi-bit operand proportional to the amplitude of the time varying signal developed at the output of the pulse amplifier 36.

The microprocessor is also programmed to compute the percentage oxygen saturation. More particularly, if $Y_R$ and $Y_{IR}$ are the logarithmic peak-to-peak values due to the red and infrared samples, respectively, then the ratio $(Y_R/Y_{IR})$ is equal to the ratio of the absorption of the arterial blood components. The $O_2$ saturation can then be computed in accordance with the Lambert-Beer law equation:

$$\text{Sat. O}_2 = \frac{A\left(\frac{Y_R}{Y_{IR}}\right) + B}{C\left(\frac{Y_R}{Y_{IR}}\right) + D}$$

where A, B, C and D are constants which depend upon the specific absorption of oxygenated hemoglobin and reduced hemoglobin at the wavelengths of the red and infrared radiation used.

Because the specific coding of the program executed by the microprocessor is dependent upon the type of microprocessor used in the system, it is not deemed expedient to set out herein a specific machine code or compiler code listing, it being recognized that persons skilled in the art may readily develop a program to perform the indicated computations.

In the practice of the present invention, attention is also paid to the selection of an appropriate sampling rate whereby fluctuating signals commonly found in the environment can be aliased into a frequency outside of the range of interest, i.e., outside of the normal pulse rate for humans. For example, and as is indicated by legends on the waveforms in FIG. 3, by selecting the sampling rate so that the period of the aliased signal is an integer multiple of the sampling period, e.g., such as by choosing an input signal sampling rate of 75 Hz, the 60 Hz power line frequency appears as a 15 Hz signal which corresponds to five sample periods and which, of course, is much higher than the human pulse. This permits simple and inexpensive filtering to accurately isolate the signals of interest from noise occasioned by commonly encountered power line frequencies, such as 60 Hz, 50 Hz and 400 Hz.

This invention has been described herein in considerable detail in order to comply with the Patent Statutes and to provide those skilled in the art with the information needed to apply the novel principles and to construct and use such specialized components as required. However, it is to be understood that the invention can be carried out by specifically different equipment and devices, and that various modifications, both as to equipment details and operating procedures, can be accomplished without departing from the scope of the invention itself.

What is claimed is:

1. Apparatus for indicating the percentage of one or more constituents of arterial blood comprising, in combination:
    (a) means for sequentially directing radiation of at least two discrete wavelengths along substantially the same path through a body part carrying arterial blood;
    (b) photosensing means positioned to intercept incident radiation including that passing through said body part and any ambient radiation for producing an electrical current proportional to the instantaneous intensity of the intercepted radiation;
    (c) logarithmic amplifier means coupled to said photosensing means for producing a time varying voltage solely proportional to the log of the component of said electrical current attributable to radiation of said at least two discrete wavelengths sequentially incident upon said photosensing means and excluding said ambient radiation;
    (d) pulse amplifier means coupled to the output of said logarithmic amplifier means for amplifying said time varying voltage irrespective of the differing direct current offsets upon which the time varying voltage may be superimposed; and
    (e) means disposed in a single channel responsive to the amplified time varying voltage for computing the percentage of said one or more constituents present in said arterial blood.

2. The apparatus as in claim 1 wherein said means responsive to the amplified time varying voltage includes means for converting said amplified time varying voltage to a multi-bit digital quantity; and programmed microprocessing means for calculating predetermined parameters based upon said multi-bit digital quantity as an operand.

3. The apparatus as in claim 2 and further including output means coupled to said microprocessing means for displaying said predetermined parameters.

4. The apparatus as in claim 2 and further including alarm means operatively coupled to said microprocessing means for signaling when the calculated predetermined parameter falls below a predetermined limit value.

5. The apparatus as in claim 2 wherein said means for converting comprises:
    (a) signal integrating means having an input terminal coupled to receive said amplified time varying voltage and an output terminal;
    (b) comparator means coupled to said output terminal for detecting when the output signal on said output terminal equals a predetermined reference value;

(c) means for inhibiting said amplified time varying voltage following the integration of a predetermined sample of said time varying voltage; and (d) means for determining the time required for said output signal on said output terminal to reach said predetermined reference value following the activation of said means for inhibiting.

6. The apparatus as in claim 1 wherein said means for sequentially directing radiation of at least two discrete wavelengths includes an LED capable of emitting light in the red portion of the visible spectrum; an LED capable of emitting infrared radiation; and means in said computing means for controlling the energization and de-energization periods of said LEDs.

7. The apparatus as in claim 6 wherein said LEDs are energized and de-energized sequentially at a sampling rate which satisfies the Nyquist criteria for aliasing interference signals attributable to ambient radiation to frequencies which fall outside a predetermined band around a subject's expected heart rate.

8. The apparatus as in claim 1 wherein said photosensing means further includes an optical filtering element disposed in the path of said intercepted incident radiation for attenuating radiation having a wavelength less than the shorter of said two discrete wavelengths.

9. The apparatus as in claim 1 and further including radio frequency filtering means operatively disposed between said photosensing means and said logarithmic amplifier means for attenuating an RF interference picked up by said photosensing means.

10. The apparatus as in claim 1 wherein said logarithmic amplifier means includes:

(a) first and second operational amplifier means, each having first and second input terminals and an output terminal;

(b) first switching means coupling said output terminal of said first operational amplifier to one of said first and second input terminals of said second operational amplifier;

(c) means including a second switching means for selectively grounding the said output terminal of said first operational amplifier;

(d) a sample-and-hold circuit coupled to said one of said first and second input terminals of said second operational amplifier for storing the signal applied to one of said first and second input terminals of said first operational amplifier when said means for sequentially directing radiation of at least two discrete wavelengths is inactive and said first and second switching means are conducting; and (e) further means coupling said one of said first and second input terminals of said first operational amplifier to the output terminal of said second operational amplifier and to said output of said logarithmic amplifier means such that when said first and second switching means are non-conducting and said means for sequentially directing radiation of at least two discrete wavelengths is active, the output signal on said output of said logarithmic amplifier means is attributable only to said radiation of said at least two discrete wavelengths and not to said ambient radiation.

11. The apparatus as in claim 1 wherein said pulse amplifier means comprises:

(a) an operational amplifier having a non-inverting input terminal, an inverting input terminal and an output terminal;

(b) a feedback resistor coupling said output terminal of said operational amplifier to said inverting input terminal;

(c) a plurality of two terminal capacitors, one terminal of each being connected in common and the other terminal of each being coupled to an associated semiconductor switching device;

(d) further resistor means coupling said common connection to said inverting input terminal of said operational amplifier, the ohmic value of said feedback resistor being much larger than that of said further resistor means;

(e) means coupling said output of said logarithmic amplifier to said non-inverting input terminal of said operational amplifier; and (f) means including said computing means for sequentially turning on said semiconductor switching devices in synchronism with the sequential energization of the sources of said radiation of at least two discrete frequencies whereby the time varying components of the signals applied to said noninverting input terminal of said operational amplifier will be sequentially amplified.

* * * * *